US00PP15700P2

(12) United States Plant Patent
Boeder

(10) Patent No.: US PP15,700 P2
(45) Date of Patent: Mar. 22, 2005

(54) ***CHRYSANTHEMUM* PLANT NAMED 'IDA'**

(50) Latin Name: *Chrysanthemum morifolium*
Varietal Denomination: Ida

(75) Inventor: Mark Roland Boeder, The Hague (NL)

(73) Assignee: Chrysanthemum Breeders Association, N.V. (NL)

( * ) Notice: Subject to any disclaimer, the term of this patent is extended or adjusted under 35 U.S.C. 154(b) by 0 days.

(21) Appl. No.: 10/756,361

(22) Filed: Jan. 14, 2004

(51) Int. Cl.[7] ..... A01H 5/00
(52) U.S. Cl. ..... Plt./291
(58) Field of Search ..... Plt./291

*Primary Examiner*—Anne Marie Grunberg
(74) *Attorney, Agent, or Firm*—Parkhurst & Wendel, L.L.P.

(57) ABSTRACT

A *chrysanthemum* plant named 'Ida' characterized by its small sized blooms with pink ray florets and purple center and profilic branching; natural season flower date September 8–13; blooming for a period of 5 weeks.

2 Drawing Sheets

BACKGROUND OF THE INVENTION

'Ida' is a product of a breeding and selection program for outdoor pot mums (garden mums) which had the objective of creating new *chrysanthemum* cultivars with a decorative type flower, a natural season flower date around September. 8–13; blooming for a period of 5 weeks. The new plant of the present invention comprises a new and distinct cultivar of *Chrysanthemum* plant 'Ida' is a seedling resulting from the open pollination among groups of *chrysanthemum* cultivars maintained under the control of the inventor for breeding purposes. The new and distinct cultivar was discovered and selected as one flowering plant by Mark Roland Boeder on a cultivated field in Rijsenhout Holland in September. 2001. The female parent is identified by the code 22.0724, not patented. The female parent has similar blooms to 'Ida' but differs in the color of the ray florets, which are more deeply pink colored than in 'Ida'. The plant has been asexually reproduced by cuttings in greenhouses at Rijsenhout Holland. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
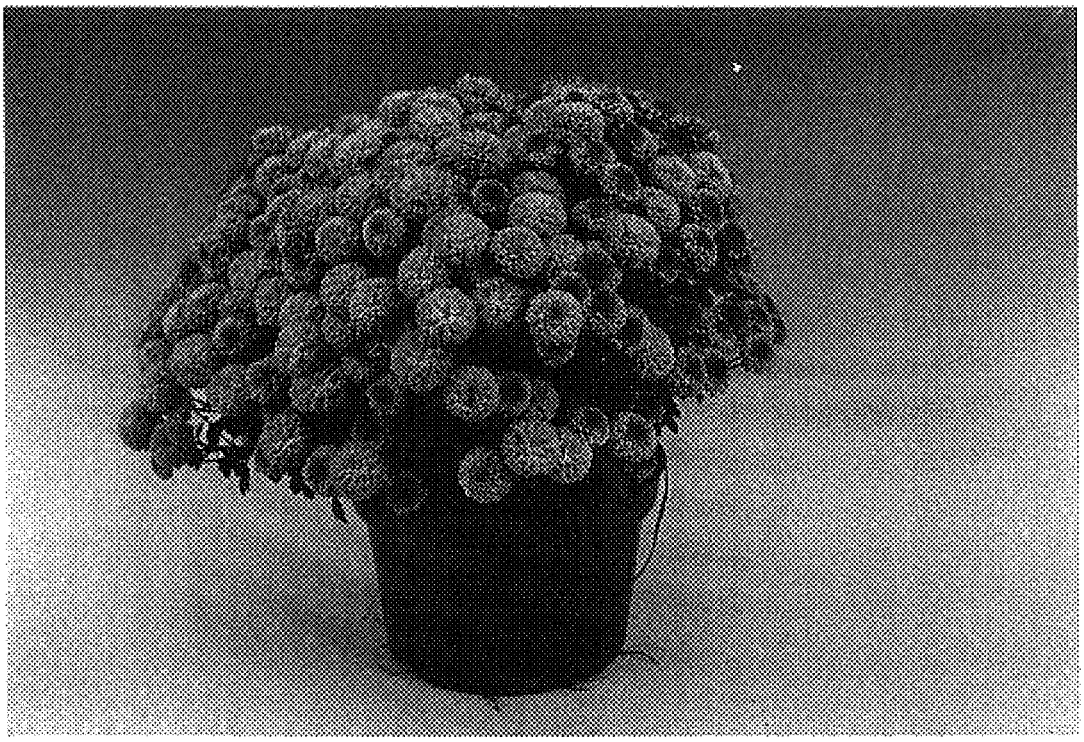
FIG. 1 shows a plant of the cultivar in full bloom.
Figure 2:
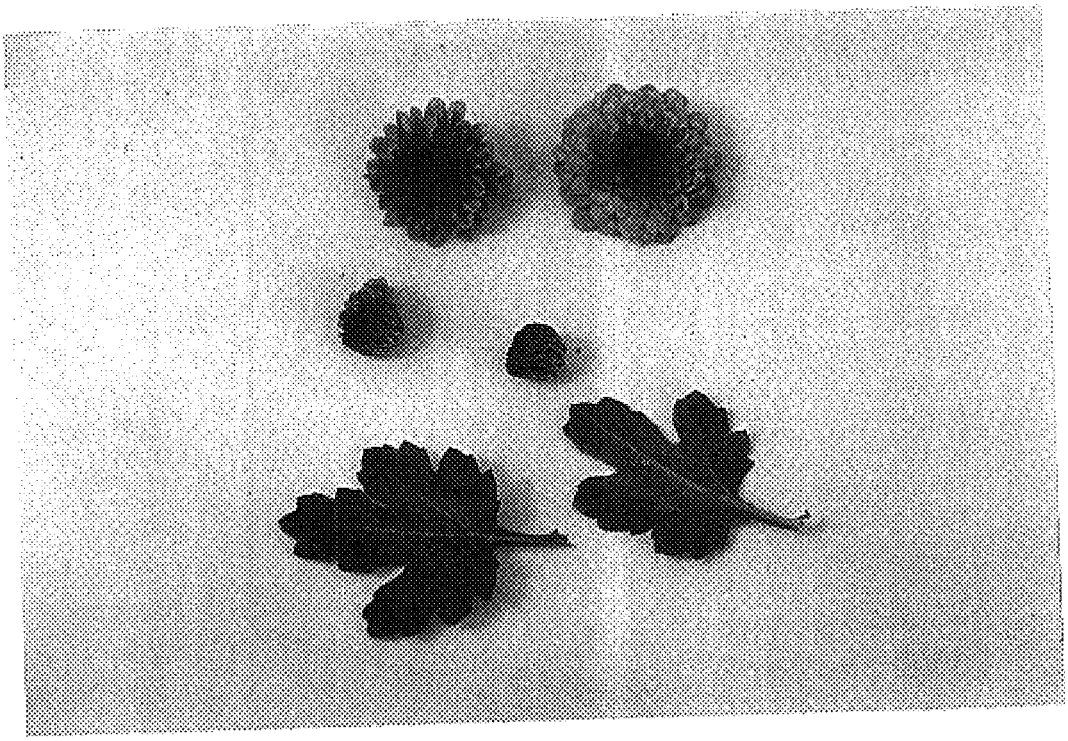
FIG. 2 shows the various stages of bloom and foliage of the new cultivar.

This new variety of *chrysanthemum* is of the botanical classification *Chrysanthemum morifolium.* The observations and measurements were gathered from plants grown out door in Rijsenhout, Holland under natural day length and temperature and planted in week 23 in 2002. The natural blooming date of this crop was September. 8–13 (week 37). The average height of the plants was 35 cms. No growth retardants were used. No tests were done on disease or insect resistance or susceptibility. No tests were done on cold or drought tolerance. This new variety produces small sized blooms with pink ray florets and a purple center blooming for a period of 5 weeks. From the cultivars known to inventor the most similar existing cultivar in comparison to 'Ida' is 'Medusa' (U.S. Plant Pat. No. 14,610). When 'Medusa' and 'Ida' are being compared the following differences are noticed: The differences of 'Medusa' and 'Ida' are (1) Flower size. The flowers of 'Medusa' are larger than those of 'Ida' (2) Number of ray florets. The number of ray florets of 'Medusa' is smaller than that of 'Ida'. (3) Color of center of immature flowers. The center of immature flowers of 'Medusa' light purple, while that of 'Ida' is deep purple.

The following is a description of the plant and characteristics that distinguish 'Ida' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

TABLE 1

Botanical Description of cultivar 'Ida'

| | |
|---|---|
| Bud | |
| Size | Small; cross-section 0.7 cm, height 0.8 cm |
| Outside Color | Yellow-green 146D |
| Involucral bracts | 2 rows, length 7 mm, width 3 mm |
| Involucral bracts among disc-florets | Not present |
| Involucral bracts color | Green 138A |
| Bloom | |
| Type | Decorative |
| Size | Small |
| Fully Expanded | 2.5 cm |
| Peduncle length | 6 cm |
| Peduncle color | Green 138B |
| Number or blooms per branch | Approx. 8 blooms per branch |
| Performance on the plant | 5 weeks |
| Seeds | Produced in small quantities, ovate grey-brown 199A, 1½ mm in length. |
| Fragrance | Typical chrysanthemum, slightly |
| Color | |
| Center of the flower | Immature Red-purple 71A<br>Mature Yellow-orange 13A. |
| Color of upper surface of the ray-florets | Purple 75D |

TABLE 1-continued

| Botanical Description of cultivar 'Ida' | |
|---|---|
| Color of the lower surface of the ray-florets | Purple 77B |
| Tonality from Distance | A garden mum with pink flowers and a purple disc |
| Color of upper side of ray florets after aging of the flowers | Purple 75D |
| Ray florets | |
| Texture | Upper and under side smooth |
| Number | 180 |
| Cross-section | Flat |
| Longitudinal axis of majority | Straight |
| Length of corolla tube | Short, 0.3 cm |
| Ray-floret margin | Entire |
| Ray-floret length | 1.4 cm |
| Ray-floret width | 0.4 cm |
| Ratio length/width | Medium |
| Shape of tip | Rounded |
| Disc florets | |
| Disc diameter | 0.3 cm |
| Distribution of disc florets | Few, visible only in mature flowers |
| Shape | Tubular |
| Color | Yellow-green 145C |
| Receptacle shape | Domed flat |
| Reproductive Organs | |
| Stamen | Present in disc florets only |
| Stamen color | Yellow-green 144A |
| Pollen | Produced in small amount |
| Pollen color | Yellow 7A |
| Styles | Thick |
| Style color | Yellow 13A |
| Style Length | 4 mm |
| Stigma color | Yellow-green 144A |
| Stigma Width | 1 mm |
| Ovaries | Enclosed in calyx |
| Plant | |
| Form | A garden mum outdoor mounded and round |
| Growth habit | Spreading |
| Growth rate | High |
| Height | 35 cm |
| Width | 50 cm |
| Stem Color | Yellow-green 147C with streaks of greyed-purple 186B |
| Stem Strength | Strong |
| Stem Brittleness | Not brittle |
| Stem Anthocyanin Coloration | Present |

TABLE 1-continued

| Botanical Description of cultivar 'Ida' | |
|---|---|
| Internode length | 1 cm |
| Length of lateral branch | From top to bottom 14 cm |
| Lateral branch color | Yellow-green 147C |
| Lateral branch, attachment | Medium strength |
| Branching (average number of lateral branches) | Good with 7 breaks after pinching |
| Natural season blooming date | September 8–13 |
| Foliage | |
| Leaf color | Upper side Green 138A<br>Under side Yellow-green 148C |
| Color midvein | Upper side Yellow-green 147D<br>Under side Yellow-green 148D |
| Size | Small; length 3.5 cm, width 2.5 cm |
| Quantity (number per lateral branch) | 16 |
| Shape | Cordiform |
| Texture upper side | Glabrous |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Truncate |
| Apex | Mucronate |
| Petiole length | 1 cm |
| Petiole color | Yellow-green 147D |

TABLE 2

| Differences with the comparison variety | | |
|---|---|---|
| | 'Ida' | 'Medusa' |
| Flower size | 2.5 cm | 4.5 cm |
| Number of ray florets | 180 | 130 |
| Color center of immature flower | Red-purple 71A | Red-purple 64D |

I claim:

1. A new and distinct variety of *chrysanthemum* plant as described and illustrated.

* * * * *